United States Patent [19]

Stamm et al.

[11] Patent Number: 5,725,872
[45] Date of Patent: Mar. 10, 1998

[54] COMPOSITION FOR FOAMS, NOTABLY RECTAL FOAMS, AND FOAMS THUS OBTAINED

[75] Inventors: André Stamm, Griesheim; Sibel Fuchs neé Sibel Cepik, Geipolshiem; Pascal Wehrle, Erstein, all of France

[73] Assignee: Ferring BV, Hoofdorf, Netherlands

[21] Appl. No.: 663,049

[22] Filed: Sep. 17, 1996

[30] Foreign Application Priority Data

Dec. 14, 1993 [FR] France .................. 93 14973

[51] Int. Cl.$^6$ .................. A61F 9/02; A61K 31/615
[52] U.S. Cl. .................. 424/436; 252/363.5; 521/189; 514/166
[58] Field of Search .................. 424/436, 78.37; 252/363.5; 514/166; 521/184

[56] References Cited

U.S. PATENT DOCUMENTS 5,082,651  1/1992  Healey et al. .................. 424/45

FOREIGN PATENT DOCUMENTS 0395329  10/1990  European Pat. Off. .
0533938   3/1993  European Pat. Off. .
2647344  11/1990  France .

*Primary Examiner*—John M. Cooney, Jr.
*Attorney, Agent, or Firm*—Fish & Richardson P.C.

[57] ABSTRACT

A composition for a foam and a process for preparing it are provided, the composition including by weight (a) more than 25% of an active ingredient in powder form; (b) from 1 to 20% of a surfactant; the balance being composed of water, wherein the powder of the active ingredient has a particle size below 20 μm. Foams, notably for rectal administration, containing this composition with a propellant gas are also provided.

64 Claims, No Drawings

5,725,872

COMPOSITION FOR FOAMS, NOTABLY RECTAL FOAMS, AND FOAMS THUS OBTAINED

BACKGROUND OF THE INVENTION

The present invention relates to novel compositions for foams, notably rectal foams, and the foams thus obtained.

Certain medicaments require local or topical administration. Thus, some medicaments require administration by oral route or rectal route, the latter case applying when the aim is to treat pathological states of the rectum or the like (astringent, disinfecting effect), for example for use in the treatment of rectal and hemorroidal inflammation, Crohn's disease, etc. In this context, it is appropriate to seek release of the active principle or ingredient at the actual region to be treated. One example of rectal treatment consists of treatment based on mesalazine, referred to as 5-ASA below, or hydrocortisone-based treatment. Thus, rectal foams containing hydrocortisone are known, and sold commercially under the names Proptocort® or Colifoam®.

Such foams are of several types. Thus, stables aqueous foams, stable non-aqueous foams, evanescent or quick-breaking aqueous foams, and quick-breaking non-aqueous foams are known. These foams can be based on emulsions or suspensions of the active principle in a pharmaceutically-acceptable carrier; the propellant gas being dispersed in the liquid phase which forms the dispersing phase.

Such foams have the advantages associated with this type of formulation, these advantages being numerous, some of them being discussed below. The pharmacological properties of foams are better than those of suppositories that suffer from the disadvantage of a release that is too late and is incomplete. Contrary to this, with rectal foams, the active principle is brought into contact with the mucous without any latency time resulting from the need for the excipient to melt or dissolve. Rectal foams also have great ease of application unlike solutions, which sometimes are not retained in the rectum, causing inconvenience to the user. Rectal foams, as they are less rigid than suppositories, readily adapt to the contours and are thus less irritating. The active principle contained in the foam, stored in a container, is in a stable form, particularly if the chemical compound is sensitive to light and/or oxidation. Pressurized foams make it possible to mask the taste of alimentary oils, which is advantageous in the case of oral administration. Such advantages justify the increased cost associated with the manufacture of such foams, which nevertheless is easy, due in part to the cost of the container, propellant gas, valves, etc.

Nevertheless, foams, in particular rectal foams, do suffer from disadvantages. Firstly, these foams contain propellant gases based on CFCs, some of which are now prohibited. Research in the field of new propellant gases makes it possible to overcome this disadvantage.

The main disadvantage of rectal foams is however their low density, which is typically of the order of 0.1 g/l which does not allow elevated amounts of an active principle to be administered. This low density makes it necessary to administer large amounts of foam which is problematical in view of the limited volume of the rectum (between about 50 ml and 400 ml). This problem can be resolved, at least in part, by the formulation of foams containing a large amount of active principle. One thus looks for foams that allow high active principle concentrations, (preferably above 30% by weight), to be used. As conventional posologies are from 1 to several grams of active principle per day, taken generally in two doses, the foam requires to have a relatively high density in order to avoid representing a volume that is too large, running the risk of provoking an expulsion reflex. For example, a foam density of at least 0.1 g/ml with 35% of filler leads to a volume of about 60 ml in order to administer 2 g of active principle. These 60 ml, compared to the volume of the rectum, do not provoke an expulsion reflex.

Depending on the type of application and the pathology to be treated, one looks for a foam that has low secondary expansion or, on the contrary, high secondary expansion. High secondary expansion is looked for if the form is required to reach the descending colon in order to then have systemic action, through passage at liver level, for example when carrying out antipyretic treatment using paracetamol in the form of a foam having systemic action. One will, on the contrary look for low secondary expansion if it is desired that the foam stay limited to a determined spot, in the preset case the lower region of the rectum for, for example, hemorrhoids treatment.

EP-A-0,395,329 in the name of Smith Kline & French Laboratories discloses foams containing 15 to 25% by weight of 5-ASA, and containing self-emulsifying waxes, glycerol, surfactants, colloidal silica and water, along with conventional additives. The 5-ASA particles have a particle size below 60 µm. The colloidal silica is present in an amount less than 1% by weight, the self-emulsifying wax being present in an amount less than 2% by weight. However, this type of formulation does not make it possible to obtain high active principle charging or filling rates, in other words higher than 30% by weight.

SUMMARY OF THE INVENTION

The present invention thus has the aim of providing a composition for foams, notably those intended for use in therapeutic treatment, which enable active principle concentrations higher than 25% to be obtained. This composition for foams is a foam concentrate, in other words the pharmaceutical carrier added to the propellant gas.

Thus, the present invention provides a composition for a foam, comprising, by weight based on the total weight of said composition:

(a) more than 25% of an active ingredient in powder form;

(b) from 1 to 20% of a surfactant; and (c) the balance being composed of water;

wherein the powder of said active ingredient has a particle size below 20 µm.

The expression "the balance being composed of water" means that water is employed to arrive at a figure of 100%, with or without the various additives optionally employed, which are covered by the expression "balance composed of water". This expression "balance composed of water" also obviously covers the aqueous buffer solution that are employed such as, for example, a phosphate buffer solution which contains, apart from purified water, monopotassium phosphate, sodium hydroxide and hydrochloric acid in sufficient amounts to obtain the desired pH.

The applicant has in effect discovered that surprisingly, particles of small dimension can be present in large quantities in the compositions. Moreover, the composition according to the invention makes it possible to deliver precise doses of medicament (exact to ±10%), after passage through metering valves (of the LAB LABO type).

According to one embodiment, the particle size is less than 10 µm, advantageously about 5 to 6 µm. Such dimensions below 20 µm can be obtained by any conventional process. In the framework of the invention, the technique known as micronization is employed, in which a 25 μm dimension powder undergoes two passes through an air jet microniser.

This small dimension makes it possible to achieve high active principle concentrations, above 25%, which in the majority of cases was the extreme upper limit with formulations according to the prior art.

The applicant has also discovered that, surprisingly, particularly advantageous results can be obtained with an active principle that has a particular bulk density.

Thus, according to one embodiment the active ingredient in powder form has a density comprised between 250 and 450 g/dm$_3$.

Advantageously, the active ingredient in powder form has a density comprised between 300 and 350 g/dm$_3$, for example about 320 g/dm$^3$.

In a preferred embodiment, the active ingredient makes up from 30 to 50% by weight of said composition and advantageously from 35 to 45% by weight of said composition.

The surfactant present in this composition enables a suspension in the form of a foam to be obtained, the gas becoming dispersed in the liquid under the effect of the surfactant. The term surfactant here also covers mixtures of surfactants.

According to one embodiment, the surfactant represents from 5 to 10% by weight of the composition, advantageously about 7.5%.

As stated previously, high or, on the contrary, low secondary expansion can be required.

When high secondary expansion is required, conventional surfactants that are known can be employed to achieve this effect, such as self-emulsifying waxes such as lanol, etc. Indeed nearly all surfactants lead to more or less pronounced expansion.

On the contrary, to date almost no formulation exists offering low secondary expansion. According to one alternative embodiment of the invention, a foam having a low secondary expansion is provided.

According to this alternative embodiment, the present invention provides a surfactant is a mixture of two surfactants, one of said surfactants being a hydrophilic surfactant having an HLB value above 10, the other being a polyoxyalkylene.

In one preferred embodiment, the hydrophilic surfactant has an HLB value above 12 and advantageously above 15.

One valuable hydrophilic surfactant is represented by polysorbate.

In one preferred embodiment, the polyoxyalkylene-based surfactant is a poloxamer. This term as used in the present invention is used to describe polymers whose structure is identical or similar to that of polymers known under the trade name Poloxamer®. The poloxamers are polymers containing polyoxyethylene and polyoxypropylene units, arranged in an appropriate sequence. This poloxamer advantageously has a molecular weight above 5,000.

The poloxamers are described in detail in Martindale (28th Ed.; page 375–376) and in USP XXII/N.F.XVII (pages 1960–61). A preferred poloxamer is the poloxamer 188 (Pluronic® F68).

The weight ratio between these two hydrophilic and polyoxyalkylene surfactants varies to a large extent. However, compositions are preferred in which the hydrophilic/polyoxyalkylene surfactant weight ratio is comprised between 1 and 5, advantageously being about 3.

According to one embodiment, the surfactant is a non-ionic surfactant. Non-ionic surfactants are less irritating.

According to one embodiment, the present composition further comprises a suspension-forming agent.

According to one embodiment, the present composition further comprises a muco-adhesive agent. This mucoadhesive agent ensures optimum bringing into contact and uniform distribution of the foam, for example in the rectum. A muco-adhesive agent that can be employed in the present invention is sodium carboxymethylcellulose, referred to below as sodium CMC or simply CMC. CMC has the further advantage of being a suspension-forming agent.

Furthermore, the present composition can additionally comprise conventional additives and additions. Such additives are present in conventional proportions and do not interfere with the physical properties sought for the foam; the conventional proportions for such additives are from 0.01 to 1% by weight based on the weight of the composition. Such additives are preservative agents and the like. From such additives, we can mention, without this being limiting, sodium benzoate, sodium EDTA and sodium metabisulfite.

The active principle that the present compositions may contain is any active principle that is insoluble in water or, on the contrary, water-soluble. In the latter case, solubility is not sufficient for all the active principle to be rendered soluble, one being then at the limit of solubility, the reminder of the active principle being then considered as insoluble. Examples of active principles which may be incorporated in the present compositions and thus in foams are, by way of non-limiting example: fluticazone, beclomethazone, budesonide, ipsalazine, balsalazine, olsalazine, mesalazine (5/ASA), 4-ASA, salazopyrine, steroids such as hydrocortisone, prednisolone, and local anaesthetics.

According to one embodiment, the active principle is 5-ASA.

Although it is possible to incorporate into the present compositions polyols such as PEG 400, glycol, glycerol and so on, the present invention makes it also possible to avoid using such polyols which are sometimes irritating.

The present invention also relates to foams, in other words to the final product directly usable by the patient. Thus, the invention also relates to a foam comprising, per 100 parts by weight of foam:

from 80 to 95 parts of the composition according to the invention; and from 5 to 25 parts of a propellent gas.

This propellent gas is any known propellent gas suitable for this application. The propellent gas is, conventionally, suitable when it leads to an internal pressure comprised between 3 and 5 kg, and when it represents from 5 to 25% of the foam, preferably from 10 to 15% by weight based on the total weight of the foam. Currently, one known propellent gas is a 12/114, 40/60 (vol/vol) mixture, the naming scheme being the one known for chlorofluorocarbons (CFC). Currently, new propellent gases are under development and will replace the CFCs. The compositions according to the invention are also suitable for forming foams with these new gases. As an example of substitution gases, isobutane can be cited.

The foams according to the present invention are suitable for any therapeutic treatment that requires topical application.

According to one embodiment, the invention provides foams for rectal application.

The present invention also relates to processes for preparing the novel compositions, and foams containing them.

Thus, the invention also relates to a process for preparing a composition according to the invention, comprising the step of dispersing powder of the active principle in water.

This dispersion step is important. In effect, as the active principle is in powder form with an extremely fine particle size, its bulk or apparent volume is extremely high. Thus, the bulk volume of the powder represents 5 times or even up to 10 times the volume of water in which said active principle is dispersed. It is thus necessary to employ an effective dispersant. In the present case, a die homogenizer of the "Gann Emulgor" type is employed. In this present specification the terms dispersion and homogenization are employed in an equivalent fashion.

According to one embodiment, the process for preparing the present composition comprises the steps consisting of:

(i) preparing a buffer;

(ii) adding and mixing a muco-adhesive agent if present;

(iii) adding and mixing conventional additives, if present;

(iv) in parallel with the preceding steps, preparing a surfactant;

(v) mixing the product of step (iii) and the product of step (iv);

(vi) adding and dispersing the powder of the active ingredient.

In one alternative embodiment, the surfactant is obtained by mixing two surfactants, one of which is a hydrophilic surfactant with a HLB higher than 10 and the other of which is a polyoxyalkalene.

The final foams are obtained conventionally by filling containers with the present composition, fitting valves to said containers, with pressurization by propellent gases, and optionally secondary packaging such as labelling operations, etc.

DETAILED DESCRIPTION OF PREFERRED EMBODIMENTS

The invention will be now described in more detail in the description and examples that follows, provided by way of illustration and which in no way should be considered as limiting the scope of the invention which may include numerous alternative embodiments readily accessible to those skilled in the art.

Below, we provide the various characteristics of the concentrate for the foam, in other words the composition for the foam. In what follows, the concentrate and the composition according to the invention are used as equivalent terms.

Variables related to composition:

Viscosity:

A Haake rotating viscosimeter (Viscosimeter Rotovisco RV 3) is employed for determining the viscosity of the concentrates or compositions. Shear strengths are measured as a function of shear speed gradient. The temperature is stable (30°±0.5° C.) in all the tests.

Appearance of the composition:

The macroscopic appearance of the concentrate was evaluated subjectively taking account of the homogeneity of the foam, the presence of lumps, viscosity, etc. An overall score for appearance (between 0 and 1, 0 being bad and 1 being good) was than assigned to each concentrate. This evaluation is superfluous for concentrates containing micronised 5-ASA of 6 μm dimension, as all the concentrates obtained are homogenous and obtained a score of 1.

Sedimentation:

Sedimentation is studied in a test tube after 48 hours. A percentage of sedimentation S is calculated from the ratio of heights of the separated phase and total height, as indicated by the following mathematical formula:

$$S\% = 1 - \frac{\text{height of sedimentation}}{\text{total height}} \times 100$$

Variables relating to the foam:

A foam was packaged using a conventional pressurisation procedure which is explained later.

Appearance:

The foam's appearance received a score on the 4 following different criteria:

noise homogeneity initial expansion collapse

Scoring was subjective, a score being given between 0 and 1 for each criterion, 0 being poor and 1 being good. Points were scored as follows:

| | | | |
|---|---|---|---|
| Noisy discharge: | 0 | silent discharge: | 1 |
| Non-homogenous appearance: | 0 | homogenous appearance: | 1 |
| Low initial expansion: | 0 | good initial expansion | 1 |
| Rapid collapse: | 0 | slow collapse: | 1 |

The total score (out of 4), takes account of these 4 values.

Secondary expansion:

The measuring tests were not carried out in graduated test tubes as expansion is too fast and intense to allow reproducible measurement. The formulations submitted to test did not exhibit secondary expansion. Expansion is thus scored in a qualitative manner with the appearance of the foam.

Evaporation in the ambient air:

For this, an empty Petri dish of known volume is employed. This space is filled with excess foam, which is immediately flattened off with a spatula. The complete thing was then placed in the ambient air at constant temperature and sheltered from draughts. The percentage of loss of weight as a function of time (based on the initial weight) was noted every 5 min over one hour. Evaporation is given by the measurement after one hour, expressed in g/100 g.

Spread:

For measuring this, 2 glass plates of size 20×20 cm, carefully degreased, are employed. An exactly weight amount (1 g) of foam is deposited in the middle of the lower plate. Following this, the upper plate which weighed 126 g, was placed on the first. The foam that is trapped between the two plates spreads out. The radius in cm of the foam circle thus obtained is noted after 3 min. The measurement is a way of evaluating consistency.

Drainage:

The amount of drainage liquid is determined: a glass funnel containing a predetermined amount of foam is placed over a graduated 5 ml test tube to enable the volume of liquid lost by drainage to be read. In order to avoid evaporation of the foam, a glass plate was placed over the funnel. Measurement was done on a test sample of 5 g of foam; the volume of liquid in the test tube was read after 24 h.

Density:

Density was measured using a funnel linked by a plastic tube to a push button able to be fitted onto a pressurized container. The weight of the complete assembly empty and the weight of the volume of water that this complete assembly (funnel+tube+push button) can contain were accurately determined in advance. Filling of the device was done by fixing the push button onto the valve of the container; this system ensures uniform filling of the funnel and the absence of air bubbles.

EXAMPLES 1 TO 33

Comparative Examples

In these examples, the active principle was replaced by talc, this being a non-oxidisable product unlike 5-ASA, having substantially the same particle size and the same physical behavior as the latter. The mean particle size of the talc was 25 µm. A comparative table is given below comparing talc and 5-ASA, justifying that their theological behaviors are comparable.

TABLE 1

|  | bulk density | packed bulk density | Hausner ratio |
|---|---|---|---|
| talc | 40 | 57.1 | 0.70 |
| 5-ASA | 61.9 | 77.6 | 0.80 |

Data on compositions F1 to F33 are given below in groups, respectively F1 to F11, F12 to F21, F22 to F33. In the tables that follow, the data are expressed in grams of product, for a total weight of 100 g.

The various formulations contain two principal vehicles, water and glycolic derivatives. Hydrophilic constituents are introduced into the water and lipophilic constituents are added to the glycol or similar products. The manner of preparation is as follows:

Dissolving the soluble salts: sodium metabisulfite, parabene, sodium edetate in the aqueous phase followed by dispersion of the colloidal silica;

incorporation of the polysorbate 20 and 80 in the glycolic phase;

separate heating of the two solutions to 65° C. followed by dispersion of the powder in the polyol, using a magnetic stirrer;

mixing the two solutions hot (the aqueous solution is poured into the glycolic solution) while stirring until completely cooled;

packaging of the suspension in flasks, the solution being poured into the container after which the valve was crimped, the gas being introduced through the valve; filling with gas was done on a Cel 3® (Coster S.A.) pressurisation unit.

The same preparation procedure was applied without exception for all the formulae, even those that did not contain one or other of the components.

For these 33 examples according to the prior art, the characteristics stated above were determined:

appearance of the suspension: homogenous and stable and sufficiently viscous to allow pressurization;

for the foams: zero, slight or large expansion, consistency (liquid or firm), behavior at ejection (good behavior or noisy discharge).

It will be noted that certain compositions are not suitable, notably F1 to F16, F19, F21 to F23, F25 to F30, and F32, as these compositions do not allow pressurization. The concentrates that were pressurized to lead to a foam were thus F17, F18, F20, F24, F31 and F33. All the foams obtained from these compounds, with the exception of the one obtained from composition F33, exhibited considerable expansion and were liquid. Only the foam obtained from composition F33 is compact and slightly expansive.

Moreover, it should be noted that these formulations only allow a filling or charging rate of 20%.

consisting of:

(i) preparing a buffer;

(ii) adding and mixing a muco-adhesive agent if present;

(iii) adding and mixing conventional additives, if present;

(iv) in parallel with the preceding steps, preparing a surfactant;

(v) mixing the product of step (iii) and the product of step (iv);

(vi) adding and dispersing the powder of the active ingredient.

EXAMPLES 34 TO 41

Comparative Examples

Next, formulations containing an active principle are prepared. Here, 5-ASA the main characteristics of which have been given above is used. 5-ASA is obtainable from Nobel Chemicals. 5-ASA has a density of about 319 g/dm$_3$. The procedure of the preparing of the foams is identical to that employed for preparing the formulations F1 to F33 except for the fact that a Polytron® apparatus (at speed 3 on the dial for 2 min was used in order to obtain a homogenous mass.

Table 3 below gives details of the compositions.

The characteristics of these foams are given below:

The foams obtained from compositions F34 and F35 are slightly expansive, and have a compact and solid appearance. The foams obtained from composition F36 and F37 also have a compact and solid appearance but their discharge is difficult as the concentrate is extremely viscous and, moreover, they exhibit considerable expansion. The foams obtained from compositions F38 and F40 expand considerably. The foam obtained from composition F39 is compact, stable and only slightly expansive. The foam obtained from composition F41 is slightly expansive but exhibits large bubbles and is slightly liquid.

EXAMPLES A1 TO A12

Comparative

The concentrates were prepared as above, followed by preparation of foams from these. The procedures used are those as discussed above. Table 4 below gives the results.

The characteristics of these foams are summarized below:

Concentrates A1 to A5 and A9 do not allow pressurization, due either to a lack of stability of the concentrate (through it sedimenting out), or because of excessive viscosity.

Concentrates A6, A7, A8, All lead to liquid foams.

The foam obtained from concentrate A10 does not behave well at discharge.

EXAMPLES OP1 to OP23

Formulations OP1 to OP23 were prepared as above. Examples OP1, OP2 to OP5 and OP6 are comparative examples, particle size being 25 µm, whereas the particle dimension for example OP3, OP4 and OP7 to OP23 is about 6 µm.

The compositions and characteristics OP1 to OP8 are summarized in table 5 below. The propellent gas is a F114/F12 mixture in a variable weight ratio and representing from 15 to 20% by weight of the final foam. The respective pressures obtained with these mixtures are given in table 5.

In the case of formulations OP9 to OP23, the PEG 400 was omitted, the particle diameter was set to about 6 μm, the pressure in the container was maintained at about 5 atm. The weight ratio between the polysorbate 80 and the Pluronic® F68 was kept at about 3.

The compositions and the characteristics of the formulations OP9 to OP23 are summarized in table 6 below.

Two criteria are employed, stability of the suspension and appearance of the foam. Scoring was done by a panel of experts; the table gives the average value of the scores assigned by the judges. Appearance was judged on a scale up to 4, rather than on the scale up to 1. The score takes account of the following criteria:

noise: during ejection of the foam from the container, absence of noise scored 1; presence of noise scored 0;

homogeneity: this characteristic of the foam was evaluated in a macroscopic manner by comparing the sizes of the various bubbles, the foam requiring to have a structure that was as regular as possible in order to obtain a score of 1; a score of 0 represented, on the contrary, poor homogeneity;

expansion: an aerated, firm and rich foam received the score 1, a foam that was poorly expansive and liquid received a score of 0;

collapse: correct behaviors received the score of 1 whereas pronounced collapse after 2 min received a score of 0.

It should be noted that the foams according to the invention allow an elevated level of charge or filling, while ensuring excellent properties for the foam.

EXAMPLE S1

The following composition was prepared, firstly for laboratory scale amounts and then for amounts on a 1 kg scale of the composition. Table 7 below gives the proportions.

TABLE 7

| Component | S1 |
|---|---|
| 5-ASA | 40.58 |
| sodium CMC | 0.9 |
| polysorbate 80 | 5.63 |
| Pluronic F68 | 1.88 |
| Sodium benzoate | 0.2 |
| sodium EDTA | 0.1 |
| sodium metabisulfite | 0.13 |
| pH 4.5 buffer | 50.58 |

The operating procedure employed for the laboratory scale preparations was as follows:

preparation of phosphate buffer with pH 4.5 (according to PF Xth Ed. page VII.1.3. "Buffer Solutions");

weighing out of the sodium carboxymethylcellulose (sodium CMC);

incorporation of the sodium CMC into the buffer, the solution being stirred by magnetic bar for 60 min;

weighing out of the preservatives; they ar weighed separately and collected in a stainless steel cup;

addition of the preservatives to the sodium CMC solution, once the latter is completely homogenous; (it is advisable to not add the preservatives before the sodium CMC as this would lead to an increase in swelling time of the solution);

weighing out of the surfactants followed by stirring with a magnetic bar in a beaker;

addition of the surfactants to the solution when the preservatives have been correctly dissolved with stirring for 15 min;

weighing out of the 5-ASA and incorporation thereof in small amounts into the solution obtained, the mixture becoming thicker and thicker, the mixture being continued to be worked with a spatula;

transfer of the concentrate obtained into a "Gann Emulgor" die homogeniser, taking care not to tighten the die too much as to break the structure of the CMC, the latter conferring a degree of stability to the preparation; homogenization is done in one single pass;

filling the flasks with an amount of 70 g per flask;

fitting and crimping of the valve;

pressurisation of the recipient with a F12/F114 freon mixture (in a 40/60 weight ratio, the gas representing about 15% of the final weight of the preparation);

packaging of the glass flask in aluminium sheet to protect the solution from light.

The operations employed for preparation on a 1 kg scale are as follows:

preparation of phosphate buffer with pH 4.5 (according to PF Xth Ed. page VII.1.3. "Buffer Solutions");

weighing out of the sodium carboxymethylcellulose (sodium CMC);

incorporation of the sodium CMC into the buffer, the solution being stirred at 3500 rpm in a "Stephan" type high speed mixer for 45 min;

weighing out of the preservatives; they ar weighed separately and collected in a stainless steel cup;

addition of the preservatives to the sodium CMC solution, once the latter is completely homogenous; (it is advisable to not add the preservatives before the sodium CMC as this would lead to an increase in swelling time of the solution);

weighing out of the surfactants followed by stirring with a magnetic bar in a beaker;

addition of the surfactants to the solution when the preservatives have been correctly dissolved with stirring for 15 min;

weighing out of the 5-ASA and incorporation thereof in small amounts into the solution obtained, the mixture becoming thicker and thicker, the mixture being continued to be worked with a spatula;

transfer of the concentrate obtained into a "Gann Emulgor" die homogeniser, taking care not to tighten the die too much as to break the structure of the CMC, the latter conferring a degree of stability to the preparation; homogenization is done in one single pass;

the remainder of the procedure is identical to that stated above.

EXAMPLE S2

The procedure as in the example above is followed, but using the formulation and the gas given in table 8 below. This formulation, using isobutane, is suitable for respecting the new regulations in force, forbidding the use of CFCs as propellent gas.

In table 8 below, the percentage weight proportions are given, with the exception of the pressurisation additive (given in bar).

TABLE 8

| Component | function | % by weight |
|---|---|---|
| 5-ASA | active principle | 38.35 |
| sodium carboxymethyl cellulose D | viscosity enhancer | 0.39 |
| Polysorbate 80 | surfactant | 5.32 |
| Poloxamer 188 | surfactant | 1.78 |
| Sodium benzoate | preservative | 0.19 |
| sodium EDTA | complexing agent | 0.095 |
| Sodium disulphite | anti-oxidant | 0.123 |
| pH 4.5 phosphate buffer | solvent | 48.27 |
| Isobutane | propellant gas | 5.5 |
| Nitrogen | pressurization agent | 5.5 bar |

EXAMPLE EC1

A composition was prepared according to example 2 of European Patent Application EP-A-0.395,329 in the name of Smith Kline and French Laboratories Ltd., except for the fact that the 5-ASA was employed in an amount of 30% by weight in the formulation.

In the first case, the particle size was about 25 μm, density being comprised between 300 and 350 g/dm$_3$. In order to obtain a homogenous concentrate, it was necessary to employ a "Polytron" homogeniser; however, the foam obtained was of poor quality: the concentrate being very thick, it was necessary to shake the container very vigorously before use, in order to obtain discharge, which was imperfect, of the foam.

In the second case, the particle size was about 25 μm, the density being below 250 g/dm$^3$. Manufacture was then impossible.

EXAMPLE EC2

The procedure of example EC1 was employed, but with a filling rate with 5-ASA equal to 35% by weight. The particle size of the 5-ASA was 25 μm. It was impossible to obtain a formulation regardless of the density.

These examples, EC1 and EC2, show that the teachings of EP-A-0.395,329 are insufficient to lead to the formulation containing more than 25% by weight of 5-ASA being obtained. The present invention, on the contrary, enables filling or charge rates distinctly higher than this 25% threshold to be achieved.

The present invention is not limited to the embodiments described but may be subject to numerous alternative embodiments readily accessible to those skilled in the art.

TABLE 2

| | F1 | F2 | F3 | F4 | F5 | F6 | F7 | F8 | F9 | F10 | F11 |
|---|---|---|---|---|---|---|---|---|---|---|---|
| talc | 20 | 20 | 10 | 10 | 10 | 10 | 10 | 10 | 10 | 10 | 10 |
| self-emulsifying wax lanol CTO | 0.3 | 0.3 | 0.3 | 0.3 | 0.3 | 0.3 | 0.3 | 0.3 | 0.3 | 0.3 | 0.3 |
| polysorbate 20 | 1 | 6 | 6 | 1 | 0 | 6 | 0 | 6 | 2 | 1 | 2 |
| sorbitane ester 80 | 6 | 1 | 6 | 1 | 6 | 0 | 6 | 0 | 1 | 2 | 1 |
| propylene glycol | 50 | 55 | 50 | 50 | 55 | 55 | | | | | 30.35 |
| glycerol | | | | | | | | | | | 30.35 |
| PEG 400 | | | | | | | 55 | 55 | 60.7 | 60.7 | |
| methyl parabene | 0.2 | 0.2 | 0.2 | 0.2 | 0.2 | 0.2 | 0.2 | 0.2 | 0.2 | 0.2 | 0.2 |
| propyl parabene | 0.04 | 0.04 | 0.04 | 0.04 | 0.04 | 0.04 | 0.04 | 0.04 | 0.04 | 0.04 | 0.04 |
| colloidal silica | 0.4 | 0.8 | 1 | | 0.2 | 0.2 | 0.2 | 0.2 | 0.2 | 0.2 | 0.2 |
| sodium EDTA | 0.1 | 0.1 | 0.1 | 0.1 | 0.1 | 0.1 | 0.1 | 0.1 | 0.1 | 0.1 | 0.1 |
| sodium metabisulfite | 3 | 3 | 3 | 3 | 0.3 | 0.3 | 0.3 | 0.3 | 0.3 | 0.3 | 0.3 |
| buffer q.s.p. 100 g | 18.96 | 13.96 | 23.36 | 33.36 | 25.16 | 25.16 | 25.16 | 25.16 | 25.16 | 25.16 | 25.16 |

| | F12 | F13 | F14 | F15 | F16 | F17 | F18 | F19 | F20 | F21 | F22 |
|---|---|---|---|---|---|---|---|---|---|---|---|
| talc | 10 | 10 | 10 | 10 | 10 | 10 | 10 | 10 | 10 | 10 | 10 |
| self-emulsifying wax lanol CTO | 0.3 | 0.3 | 0.5 | 1.0 | 1.5 | 2.0 | 1.5 | 1.5 | 1.0 | 1.5 | 1 |
| polysorbate 20 | 1 | 2 | 2 | 2 | 2 | 2 | 2 | 2 | 2 | 2 | |
| sorbitane ester 80 | 2 | 1 | 1 | 1 | 1 | 1 | 1 | 1 | 1 | 1 | 0.5 |
| propylene glycol | 30.35 | 30.35 | | | | | | | | | |
| glycerol | 30.35 | 30.35 | | | | | | | | | |
| PEG 400 | | | 60 | 60 | 60 | 60 | 50 | 70 | 50 | 42.5 | 50 |
| methyl parabene | 0.2 | 0.2 | | | | | | | | | |
| propyl parabene | 0.04 | 0.04 | | | | | | | | | |
| colloidal silica | 0.2 | 0.2 | | | | | | | | | |
| sodium EDTA | 0.1 | 0.1 | | | | | | | | | |
| sodium metabisulfite | 0.3 | 0.3 | | | | | | | | | |
| buffer q.s.p. 100 g | 25.16 | 25.16 | 25 | 25 | 25 | 25 | 35 | 15 | 35 | 42.5 | 35 |

| | F23 | F24 | F25 | F26 | F27 | F28 | F29 | F30 | F31 | F32 | F33 |
|---|---|---|---|---|---|---|---|---|---|---|---|
| talc | 10 | 10 | 10 | 10 | 10 | 10 | 10 | 10 | 10 | 10 | 10 |
| self-emulsifying wax lanol CTO | 1 | 1 | 1 | 1 | 1 | 1 | 1 | 1 | 1 | 1 | 1 |
| polysorbate 20 | | | | | | | | | | | |
| sorbitane ester 80 | 1.5 | 2.5 | 3.5 | 4.5 | 5.5 | 6.5 | 7.5 | 8.5 | 9.5 | 10.5 | 11.5 |
| propylene glycol | | | | | | | | | | | |
| glycerol | | | | | | | | | | | |
| PEG 400 | 50 | 50 | 50 | 50 | 50 | 50 | 50 | 50 | 50 | 50 | 50 |
| methyl parabene | | | | | | | | | | | |
| propyl parabene | | | | | | | | | | | |
| colloidal silica | | | | | | | | | | | |

TABLE 2-continued

| | | | | | | | | | | | |
|---|---|---|---|---|---|---|---|---|---|---|---|
| sodium EDTA | | | | | | | | | | | |
| sodium metabisulfite | | | | | | | | | | | |
| buffer q.s.p. 100 g | 35 | 35 | 35 | 35 | 35 | 35 | 35 | 35 | 35 | 35 | 35 |

TABLE 3

| | F34 | F35 | F36 | F37 | F38 | F39 | F40 | F41 |
|---|---|---|---|---|---|---|---|---|
| 5-ASA | 10 | 15 | 20 | 25 | 25 | 20 | 25 | 25 |
| self-emulsifying wax lanol CTO | 0.92 | 0.89 | 0.79 | 0.69 | 0.69 | 0.79 | 0.69 | 1.24 |
| polysorbate 20 | | | | | | | | 1.65 |
| polysorbate 80 | 10.52 | 10.02 | 9.52 | 8.82 | 8.82 | 9.52 | 8.82 | |
| sorbitane ester 80 | | | | | | | | 0.83 |
| propylene glycol | | | | | | | | |
| glycerol | | | | | | | | |
| PEG 400 | 45.85 | 43.18 | 40.58 | 38.18 | 37.88 | 40.28 | 37.58 | 35.12 |
| methyl parabene | 0.2 | 0.2 | 0.2 | 0.2 | 0.2 | 0.2 | 0.2 | 0.2 |
| propyl parabene | 0.04 | 0.04 | 0.04 | 0.04 | 0.04 | 0.04 | 0.04 | 0.04 |
| colloidal silica | | | | | 0.4 | 0.4 | 0.4 | 0.4 |
| sodium EDTA | 0.1 | 0.1 | 0.1 | 0.1 | 0.1 | 0.1 | 0.1 | 0.1 |
| sodium metabisulfite | 0.3 | 0.3 | 0.3 | 0.3 | 0.3 | 0.3 | 0.3 | 0.3 |
| buffer q.s.p. 100 g | 32.07 | 30.27 | 28.47 | 26.67 | 26.57 | 28.37 | 26.27 | 35.12 |

TABLE 4

| | A1 | A2 | A3 | A4 | A5 | A6 | A7 | A8 | A9 | A10 | A11 | A12 |
|---|---|---|---|---|---|---|---|---|---|---|---|---|
| 5-ASA | 35 | 35 | 35 | 35 | 35 | 35 | 35 | 35 | 35 | 35 | 35 | 35 |
| self-emulsifying wax lanol CTO | | | | | | | | | 2 | | | 1 |
| soya lecithin | 1 | 1 | 2 | 2 | 2 | 1 | 1 | | | | | |
| polysorbate 20 | | | | | | | | 1.65 | | | | |
| polysorbate 80 | | | | 6 | 6 | | | | | 5 | | |
| sorbitane ester 80 | | | | 4 | 4 | | | | | | 5 | |
| Pluronic F68 | | | | | | | | 1 | | 1 | 1 | 1 |
| propylene glycol | | | | | | | | | | | | |
| glycerol | | | | | | | | | | | | |
| PEG 400 | | | | 10 | 10 | 10 | 10 | 10 | 10 | 10 | 10 | 10 |
| CMC | | 1 | 2 | 2 | 1 | 1 | 1 | 1 | 1 | 1 | 1 | 1 |
| methyl parabene | 0.2 | 0.2 | 0.2 | 0.2 | 0.2 | 0.2 | 0.2 | 0.2 | | | | |
| propyl parabene | 0.04 | 0.04 | 0.04 | 0.04 | 0.04 | 0.04 | 0.04 | 0.04 | | | | |
| colloidal silica | | | | | | | | | | | | |
| sodium EDTA | | | | | | | | | | | | |
| Na metabisulfite | | | | | | | | | | | | |
| buffer qsp 100 g | 64 | 62 | 61 | 41 | 42 | 53 | 53 | 53 | 52 | 48 | 48 | 53 |
| F114/F12 | 60/40 | 60/40 | 60/40 | 60/40 | 60/40 | 100/0 | 0/100 | 60/40 | 60/40 | 60/40 | 60/40 | 60/40 |
| % by weight of gas | 20 | 20 | 20 | 20 | 20 | 15 | 15 | 15 | 15 | 15 | 15 | 15 |

TABLE 5

| | OP1 | OP2 | OP3 | OP4 | OP5 | OP6 | OP7 | OP8 |
|---|---|---|---|---|---|---|---|---|
| 5-ASA | 40 | 30 | 40 | 30 | 40 | 30 | 40 | 30 |
| polysorbate 80 | 8.57 | 7.5 | 7.5 | 8.57 | 7.5 | 8.57 | 8.57 | 7.5 |
| Pluronic F68 | 1.43 | 2.5 | 2.5 | 1.43 | 2.5 | 1.43 | 1.43 | 2.5 |
| CMC | 1.5 | 0.5 | 0.5 | 1.5 | 1.5 | 0.5 | 0.5 | 1.5 |
| PEG 400 | 4.85 | 5.95 | 4.95 | 5.85 | | | | |
| buffer q.s.p. 100 g | 43.65 | 53.55 | 44.55 | 52.65 | 48.5 | 59.5 | 49.5 | 58.5 |
| Concentrate | | | | | | | | |
| viscosity (mPa · s) | 6353 | 237 | 619 | 1581 | 5156 | 206 | 413 | 1485 |
| sedimentation in % | 0 | 4.6 | 0 | 0 | 0 | 1 | 0 | 0 |
| appearance (scale to 1) | 0.25 | 1 | 1 | 1 | 0.5 | 0.75 | 1 | 1 |

TABLE 5-continued

|  | OP1 | OP2 | OP3 | OP4 | OP5 | OP6 | OP7 | OP8 |
|---|---|---|---|---|---|---|---|---|
| Foam |  |  |  |  |  |  |  |  |
| container press. (atm) | 5 | 3.2 | 5 | 3.5 | 2.6 | 4.6 | 3.5 | 5 |
| density (g/ml) | 0.12 | 0.03 | 0.11 | 0.06 | 0.08 | 0.05 | 0.05 | 0.11 |
| secondary expansion |  |  |  |  |  |  |  |  |
| collapse after 3 mins. (cm) | 4.5 | 8 | 7.8 | 6.5 | 6 | 10 | 8 | 6.25 |
| evaporation in 60 min | 8 | 18.2 | 9 | 22.1 | 13.6 | 45.6 | 25.6 | 15.1 |
| drainage (ml) over 24 h | 0.3 | 0.85 | 0 | 0.1 | 0.6 | 1.35 | 0.1 | 0.1 |
| appearance (scale to 1) | 0.125 | 1 | 0.125 | 0.75 | 0.25 | 0.5 | 0.5 | 0.25 |

TABLE 6

|  | OP9 | OP10 | OP11 | OP12 | OP13 | OP14 | OP15 | OP16 |
|---|---|---|---|---|---|---|---|---|
| 5-ASA | 30 | 40 | 30 | 40 | 30 | 40 | 30 | 40 |
| polysorbate 80 | 3.75 | 3.75 | 3.75 | 3.75 | 7.5 | 7.5 | 7.5 | 7.5 |
| Pluronic F68 | 1.25 | 1.25 | 1.25 | 1.25 | 2.5 | 2.5 | 2.5 | 2.5 |
| CMC | 0.5 | 0.5 | 1.5 | 1.5 | 0.5 | 0.5 | 1.5 | 1.5 |
| buffer qsp 100 g | 64.5 | 54.5 | 63.5 | 53.5 | 59.5 | 49.5 | 58.5 | 48.5 |
| Concentrate |  |  |  |  |  |  |  |  |
| viscosity (mPa · s) | 94 | 291 | 766 | 2733 | 139 | 486 | 917 | 4263 |
| sedimentation (%) | 3.45 | 2.33 | 0.66 | 0 | 3.53 | 2.65 | 0.71 | 0 |
| appearance (scale to 1) |  |  |  |  |  |  |  |  |
| Foam |  |  |  |  |  |  |  |  |
| densite (g/ml) | 0.04 | 0.06 | 0.06 | 0.12 | 0.05 | 0.07 | 0.12 | 0.29 |
| secondary expansion |  |  |  |  |  |  |  |  |
| collapse after 3 min (cm) | 9.1 | 7.2 | 6 | 44.4 | 8.4 | 6.7 | 5.5 | 3.8 |
| evaporation over 60 min (g/100 g) | 34.17 | 40.12 | 36.03 | 25.03 | 37.91 | 29.35 | 23.28 | 15.48 |
| drainage (ml) over 24 h |  |  |  |  |  |  |  |  |
| appearance (on a scale from 0 to 1) |  |  |  |  |  |  |  |  |

|  | OP17 | OP18 | OP19 | OP20 | OP21 | OP22 | OP23 |
|---|---|---|---|---|---|---|---|
| 5-ASA | 35 | 41.08 | 28.93 | 35 | 35 | 35 | 35 |
| polysorbate 80 | 5.63 | 5.63 | 5.63 | 5.63 | 5.63 | 7.91 | 3.35 |
| Pluronic F68 | 1.88 | 1.88 | 1.88 | 1.88 | 1.88 | 2.64 | 1.12 |
| CMC | 1 | 1 | 1 | 1.61 | 0.39 | 1 | 1 |
| buffer qsp 100 g | 56.5 | 50.41 | 62.56 | 55.88 | 57.10 | 53.45 | 59.53 |
| Concentrate |  |  |  |  |  |  |  |
| viscosity (mPa · s) | 626 | 2178 | 343 | 2159 | 169 | 839 | 531 |
| sedimentation (%) | 0.86 | 0 | 3.77 | 0 | 3.57 | 0.82 | 2 |
| appearance (scale to 1) |  |  |  |  |  |  |  |
| Foam |  |  |  |  |  |  |  |
| density (g/ml) | 0.10 | 0.10 | 0.05 | 0.08 | 0.05 | 0.07 | 0.06 |
| secondary expansion |  |  |  |  |  |  |  |
| collapse after 3 min (cm) | 6 | 5.29 | 7.03 | 5.06 | 7.58 | 5.87 | 6.32 |
| evaporation over 60 min (g/100 g) | 28.48 | 17.61 | 27.91 | 19.83 | 32.77 | 22.35 | 27.50 |
| drainage in ml over 24 h |  |  |  |  |  |  |  |
| appearance (on a scale from 0 to 1) |  |  |  |  |  |  |  |

What is claimed is:

1. A composition for a foam, comprising, by weight based on the total weight of said composition:

(a) more than 25% of mesalazine as an active ingredient in powder form;

(b) from 1 to 20% of a surfactant; and (c) water;

wherein the powder of said mesalazine active ingredient has a particle size below 20 μm and has a density of between 250 and 450 g/dm³.

2. The composition according to claim 1, in which said particle size is below 10 μm.

3. The composition according to claim 1, in which the active ingredient in powder form has a density of between 300 and 350 g/dm³.

4. The composition according to claim 2, in which the active ingredient in powder form has a density of between 300 and 350 g/dm³.

5. The composition according to claim 1, in which active ingredient makes up from 30 to 50% by weight of said composition.

6. The composition according to claim 2, in which the active ingredient makes up from 30 to 50% by weight of said composition.

7. The composition according to claim 3, in which the active ingredient makes up from 30 to 50% by weight of said composition.

8. The composition according to claim 4, in which the active ingredient makes up from 30 to 50% by weight of said composition.

9. The composition according to claim 5, in which the active ingredient makes up from 35 to 45% by weight of said composition.

10. The composition according to claim 6, in which the active ingredient makes up from 35 to 45% by weight of said composition.

11. The composition according to claim 7, in which the active ingredient makes up from 35 to 45% by weight of said active composition.

12. The composition according to claim 8, in which the active ingredient makes up from 35 to 45% by weight of said composition.

13. The composition according to claim 1, in which said surfactant makes up from 5 to 10% by weight of said composition.

14. The composition according to claim 7, in which said surfactant makes up from 5 to 10% by weight of said composition.

15. The composition according to claim 3, in which said surfactant makes up from 5 to 10% by weight of said composition.

16. The composition according to claim 4, in which said surfactant makes up from 5 to 10% by weight of said composition.

17. The composition according to claim 1, in which said surfactant is a mixture of two surfactants, one of said surfactants being a hydrophilic surfactant having an HLB value above 10, the other being a polyoxyalkylene.

18. The composition according to claim 2, in which said surfactant is a mixture of two surfactants, one of said surfactants being a hydrophilic surfactant having an HLB value above 10, the other being a polyoxyalkylene.

19. The composition according to claim 3, in which said surfactant is a mixture of two surfactants, one of said surfactants being a hydrophilic surfactant having an HLB value above 10, the other being a polyoxyalkylene.

20. The composition according to claim 4, in which said surfactant is a mixture of two surfactants, one of said surfactants being a hydrophilic surfactant having an HLB value above 10, the other being a polyoxyalkylene.

21. The composition according to claim 17, in which said hydrophilic surfactant has an HLB value above 12.

22. The composition according to claim 18, in which said hydrophilic surfactant has an HLB value above 12.

23. The composition according to claim 19, in which said hydrophilic surfactant has an HLB value above 12.

24. The composition according to claim 20, in which said hydrophilic surfactant has an HLB value above 12.

25. The composition according to claim 17, in which said hydrophilic surfactant is polysorbate.

26. The composition according to claim 18, in which said hydrophilic surfactant is polysorbate.

27. The composition according to claim 19, in which said hydrophilic surfactant is polysorbate.

28. The composition according to claim 20, in which said hydrophilic surfactant is polysorbate.

29. The composition according to claim 17, in which said polyoxyalkylene-based surfactant is a poloxamer.

30. The composition according to claim 18, in which said polyoxyalkylene-based surfactant is a poloxamer.

31. The composition according to claim 19, in which said polyoxyalkylene-based surfactant is a poloxamer.

32. The composition according to claim 20, in which said polyoxyalkylene-based surfactant is a poloxamer.

33. The composition according to claim 29, in which said polyoxyalkylene-based surfactant has a molecular weight above 5,000.

34. The composition according to claim 30, in which said polyoxyalkylene-based surfactant has a molecular weight above 5,000.

35. The composition according to claim 31, in which said polyoxyalkylene-based surfactant has a molecular weight above 5,000.

36. The composition according to claim 32, in which said polyoxyalkylene-based surfactant has a molecular weight above 5,000.

37. The composition according to claim 17, in which the hydrophilic/polyoxyalkene surfactant weight ratio is between 1 and 5.

38. The composition according to claim 18, in which the hydrophilic/polyoxyalkene surfactant weight ratio is between 1 and 5.

39. The composition according to claim 19, in which the hydrophilic/polyoxyalkene surfactant weight ratio is between 1 and 5.

40. The composition according to claim 20, in which the hydrophilic/polyoxyalkene surfactant weight ratio is between 1 and 5.

41. The composition according to claim 1, in which said surfactant is a non-ionic surfactant.

42. The composition of claim 2, in which said surfactant is a non-ionic surfactant.

43. The composition of claim 3, in which said surfactant is a non-ionic surfactant.

44. The composition of claim 5, in which said surfactant is a non-ionic surfactant.

45. The composition of claim 1, further comprising a muco-adhesive agent.

46. The composition of claim 2, further comprising a muco-adhesive agent.

47. The composition of claim 3, further comprising a muco-adhesive agent.

48. The composition of claim 4, further comprising a muco-adhesive agent.

49. A composition for a foam, comprising, by weight based on the total weight of said composition:
  (a) from 30 to 50% of mesalazine as an active ingredient in powder form;
  (b) from 1 to 20% of a surfactant; and
  (c) the balance being composed of water and optional additives and adjuvants;
  wherein the powder of said mesalazine active ingredient has a particle size below 10 μm and has a density of between 250 and 450 g/dm$^3$.

50. The composition according to claim 49, in which the active ingredient in powder form has a density of between 300 and 350 g/dm$^3$.

51. The composition according to claim 49, in which said surfactant makes up from 5 to 10% by weight of said composition.

52. The composition according to claim 50, in which said surfactant makes up from 5 to 10% by weight of said composition.

53. The composition according to claim 49, in which said surfactant is a mixture of two surfactants, one of said surfactants being a polysorbate surfactant having an HLB value above 10, the other being a poloxamer.

54. The composition according to claim 50, in which said surfactant is a mixture of two surfactants, one of said surfactants being a polysorbate surfactant having an HLB value above 10, the other being a poloxamer.

55. The composition according to claim 51, in which said surfactant is a mixture of two surfactants, one of said surfactants being a polysorbate surfactant having an HLB value above 10, the other being a poloxamer.

56. The composition according to claim 52, in which said surfactant is a mixture of two surfactants, one of said surfactants being a polysorbate surfactant having an HLB value above 10, the other being a poloxamer.

57. The composition according to claim 53, in which the polysorbate/poloxamer weight ratio is between 1 and 5.

58. The composition according to claim 54, in which the polysorbate/poloxamer weight ratio is between 1 and 5.

59. The composition according to claim 55, in which the polysorbate/poloxamer weight ratio is between 1 and 5.

60. The composition according to claim 56, in which the polysorbate/poloxamer weight ratio is between 1 and 5.

61. A foam comprising, per 100 parts by weight of foam:
from 80 to 95 parts of the composition according to claim 1, and
from 5 to 25 parts of a propellent gas.

62. A foam comprising, per 100 parts by weight of foam:
from 80 to 95 parts of the composition according to claim 49, and
from 5 to 25 parts of a propellent gas.

63. A method of treatment of a patient suffering of rectum pathologies comprising the administration through rectal route of an effective amount of the foam according to claim 61.

64. A method of treatment of a patient suffering of rectum pathologies comprising the administration through rectal route of an effective amount of the foam according to claim 62.

* * * * *